(12) United States Patent
Silverman et al.

(10) Patent No.: US 8,426,340 B2
(45) Date of Patent: Apr. 23, 2013

(54) PLANT GROWTH ENHANCEMENT WITH COMBINATIONS OF PESA AND PLANT GROWTH REGULATORS

(75) Inventors: Franklin Paul Silverman, Highland Park, IL (US); Jennifer C. Kochan, Palatine, IL (US); Asako Iida, Kobe (JP); Nicole Higgs, Racine, WI (US); Dale O. Wilson, Jr., Round Lake Beach, IL (US); Peter D. Petracek, Grayslake, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 285 days.

(21) Appl. No.: 12/763,665

(22) Filed: Apr. 20, 2010

(65) Prior Publication Data

US 2010/0267557 A1 Oct. 21, 2010

Related U.S. Application Data

(60) Provisional application No. 61/170,761, filed on Apr. 20, 2009.

(51) Int. Cl.
*A01N 25/32* (2006.01)
(52) U.S. Cl.
USPC .......................................... 504/110; 504/118
(58) Field of Classification Search ................... 504/110
See application file for complete search history.

(56) References Cited

U.S. PATENT DOCUMENTS

| | | | | |
|---|---|---|---|---|
| 3,334,991 A | * | 8/1967 | Hageman et al. | 504/226 |
| 5,935,906 A | * | 8/1999 | Callan et al. | 504/130 |
| 2003/0008949 A1 | * | 1/2003 | Devisetty et al. | 524/56 |
| 2003/0019640 A1 | | 1/2003 | Hatcher | |
| 2007/0149401 A1 | | 6/2007 | Haskell et al. | |

FOREIGN PATENT DOCUMENTS

| | | |
|---|---|---|
| JP | 11-255607 | 9/1999 |
| WO | WO 99/45774 | 9/1999 |

OTHER PUBLICATIONS

Itagaki et al. (Biological Activities and Structure-Activity Relationship of Substitution Compounds of N-[2-(1-naphthypethyl]succinamic acid, derived from a new category of root-promoting substances, N-(phenethyl)succinamic acid analogs, Plant and Soil 255: 67-75, 2003).*
Takahashi et al. (Ethylene Promotes the Induction by Auxin of the Cortical Microtubule Randomization Required for Low-pH-Induced Root Hair Initiation in Lettuce Seedlings, Plant Cell Physiol. 44(9): 932-940).*
Cantliffe, "Benzyladenine in the priming solution reduces thermodormancy of lettuce seeds", HortTechnology, Oct./Dec. 1991 pp. 95-97.
Soejima et al., 609(2pK03) "Biological activities of root-promoting substance, N-(phenethyl)succinamic acid, and its structure-activity relationship", Plant Cell Physiol. vol. 41, Supplement (2000), pp. s197.
Blaauw-Jansen "Differences in the nature of thermodormancy and far-red dormancy in lettuce seeds", Physiol. Plant 53 Copenhagen 1981, pp. 553-557.
D. J. Cantliffe, "Benzyladenine in the priming solution reduces thermodormancy of lettuce seeds", HortTechnology Oct./Dec. 1991, pp. 95-97.
Soejima et al., "Biological activities of root-promoting substance, N-(phenethyl)succinamic acid, and its structure-activity relationship", Plant Cell Physiol. vol. 41, Supplement 2000, pp. s197.
Blaauw-Jansen et al., "Differences in the nature of thermodormancy and far-red dormancy in lettuce seeds", Physiol. Plant, 53; Copenhagen 1981, pp. 553-557.

* cited by examiner

*Primary Examiner* — Fereydoun G Sajjadi
*Assistant Examiner* — Danielle Sullivan
(74) *Attorney, Agent, or Firm* — Wood, Phillips, Katz, Clark & Mortimer

(57) ABSTRACT

A combination treatment of N-(phenylethyl)succinamic acid or its salts and a plant growth regulator applied as a seed treatment or applied directly on or near the root zone of the seedling or growing plant promotes plant growth is disclosed.

15 Claims, No Drawings

PLANT GROWTH ENHANCEMENT WITH COMBINATIONS OF PESA AND PLANT GROWTH REGULATORS

FIELD OF THE INVENTION

The present invention is directed to improving plant growth using N-(phenylethyl)succinamic acid (PESA) or its salts in the presence of a plant growth regulator (PGR). This is accomplished using a combination treatment of N-(phenylethyl)succinamic acid or its salts and a PGR applied as a seed treatment or applied directly on or near the root zone of a seedling or growing plant. This invention is particularly directed to the use of PESA to improve the positive effects and counteract the negative effects of selected PGRs.

BACKGROUND OF THE INVENTION

The seeds, seedlings, and plants of crops are often treated with pesticides to control insects, nematodes, and disease organisms such as fungi and bacteria. PGRs are sometimes applied to improve the growth and development of crops. For example, semi-dwarf rice seeds are treated with gibberellic acid (GA3) to promote uniform emergence and early growth and establishment of seedlings. However, the benefits of some PGR treatments are tempered by their negative effects. For example, cytokinins such as 6-benzyladenine (6BA) can break thermodormancy of lettuce seeds, (Cantliffe, D. J., 1991, HortTechnology. 1: 95-96), but cytokinins also reduce root growth. Consequently, the overall benefit of use of cytokinins to promote lettuce germination is reduced. PESA is a recently discovered compound that reportedly promotes root growth (Soejima et al. 2000, Plant Cell Physiol. 41: 197). The effects of combinations of PESA and PGRs on plant growth have not been well documented. In particular, the use of PESA to safen the effects of high doses of PGRs has not been previously reported.

SUMMARY OF THE INVENTION

The present invention is directed to improving plant growth using N-(phenylethyl)succinamic acid or its salts, when another plant growth regulator (PGR) other than abscisic acid is used. This is accomplished by using N-(phenylethyl)succinamic acid or its salts as a seed treatment or by application directly to or near the root zone of a seedling or growing plant. Alternatively, PESA or its salts may be applied to the shoots or leaves of the plant. Because PGR treatments may differentially affect the root and shoot of the plant, less than optimal growth results in an imbalance of the root to shoot ratio. This invention may permit the use of PESA or its salts with PGRs other than abscisic acid to maintain optimal plant growth.

The present invention is also directed to a composition comprising selected PGRs and PESA or its salts.

DETAILED DESCRIPTION OF THE INVENTION

PGRs are compounds used to enhance the growth or development of crops. PGRs are typically applied as a seed treatment, foliar spray, drench, or sprench. PGR activity is typically classified based on the PGR having similar effects as naturally occurring plant hormones or the antagonism of the effects of these hormones.

PGRs are either naturally occurring or synthetic compounds which modulate plant growth and development. Suitable PGRs include, but are not limited to, cytokinins, cytokinin antagonists, gibberellin biosynthetic inhibitors, abscisic acid antagonists, ethylene biosynthetic inhibitors, ethylene action inhibitors, auxins, auxin antagonists, jasmonates, salicylates and other systemic acquired resistance inducers.

PESA is N-(2-phenylethyl)succinamic acid of the formula:

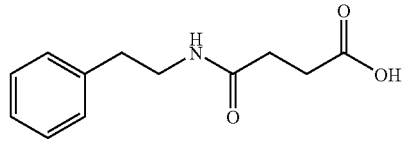 [SMILES: O=C(O)CCC(=O)NCCc1ccccc1]

which can be prepared by the method described in WO 99/45774.

In the present invention, any pesticidally acceptable salt of PESA can also be used as well as PESA. Examples of such salts include calcium, magnesium, potassium, sodium and ammonium. Organic ammonium salts include the salts formed by neutralization of PESA by amine bearing one, two or three groups selected from the group consisting of C1-C4 alkyl groups and C1-C4 hydroxyalkyl groups. Typical examples of organic ammonium salts include trimethylammonium salt, isopropylammonium salt, 2-hydroxyethylammonium salt (ethanolamine salt), 2-hydroxyethyldimethylammonium salt (dimethylethanolamine salt), bis(2-hydroxyethyl)ammonium salt (diethanolamine salt) and tris(2-hydroxyethyl)ammonium salt (triethanolamine salt). The presently preferred salt is the sodium salt.

The salts of PESA are produced, for example, by dissolving the free acid (PESA) in water and adding an equimolar amount of a base to the solution. In the case of the sodium salt, sodium hydroxide is preferably used as the base and this method allows for the production of sodium salt solutions ranging in concentration from 0.1 to 40%.

The compositions of the present invention further comprise a carrier in general, and optionally auxiliaries for formulation. Examples of auxiliaries include surfactants, dispersing agents, thickeners, stabilizing agents, antifreezing agents and colorants.

Examples of solid carriers include powders and granules of clays such as kaoline clay, diatomaceous earth, bentonite, fubasami clay and terra alba; synthetic hydrated silica; talc; ceramic; other inorganic minerals such as sericite, quartz, sulfur, activated carbon, calcium carbonate and hydrated silica; and chemical fertilizers such as ammonium sulfate, ammonium phosphate, ammonium nitrate, ammonium chloride and urea. Examples of liquid carriers include aromatic and aliphatic hydrocarbons such as xylene, toluene, alkylnaphthalene, phenylxylylethane, kerosene, gas oil, hexane and cyclohexane; halogenated hydrocarbons such as chlorobenzene, dichloromethane, dichloroethane and trichloroethane; alcohols such as methanol, ethanol, isopropyl alcohol, butanol, hexanol, benzyl alcohol and ethylene glycol; ethers such as diethyl ether, ethylene glycol dimethyl ether, diethylene glycol monomethyl ether, diethylene glycol monoethyl ether, propylene glycol monomethyl ether, tetrahydrofuran and dioxane; esters such as ethyl acetate and butyl acetate; ketones such as acetone, methyl ethyl ketone, methyl isobutyl ketone and cyclohexanone; nitriles such as acetonitrile and isobutyronitrile; sulfoxides such as dimethyl sulfoxide (DMSO); amides such as N,N-dimethylformamide, N,N-dimethylacetamide and N-methylpyrollidone; alkylydene carbonates such as propylene carbonate; vegetable oils such as soybean oil and cotton seed oil; plant essential oils such as orange oil, hyssop oil and lemon oil; and water. Examples of gaseous carriers include butane gas, flon gas, liquefied petroleum gas (LPG), dimethyl ether and carbon dioxide. When the composition contains a carrier, the amount of the carrier is usually 1 to 99% by weight of the composition.

Examples of surfactants include alkylsulfate salts, alkylsulfonate salts, alkylarylsulfonate salts such as alkylbenzenesulfonate salts and alkylnaphthalenesulfonate salts, polyoxyethylene alkyl ether phosphate salts, alkylaryl ethers, polyoxyethylene alkylaryl ethers, polyethylene glycol ethers, polyvalent alcohol esters and sugar alcohols. Examples of dispersing agents include calcium ligninsulfonate, methylcellulose and hydroxymethylcellulose.

Examples of thickeners include aluminum magnesium silicate, gum arabic, polyvinyl alcohol and polyvinylpyrrolidone.

Examples of stabilizing agents include BHT (2,6-di-tert-butyl-4-methylphenol) and BHA (mixture of 2-tert-butyl-4-methoxyphenol and 3-tert-butyl-4-methoxyphenol).

Examples of antifreezing agents include ethylene glycol, propylene glycol, trimethylene glycol, 1,2-butanediol, 1,3-butanediol, 1,4-butanediol, 1,4-pentanediol, 3-methyl-1,5-pentanediol, 2,3-dimethyl-2,3-butanediol, trimethylol propane, mannitol, sorbitol, glycerol, pentaerythritol, 1,4-cyclohexanedimethanol, xylenol, bisphenols such as bisphenol A or the like, diethylene glycol, triethylene glycol, tetraethylene glycol, polyoxyethylene or polyoxypropylene glycols of molecular weight up to about 4000, diethylene glycol monomethyl ether, diethylene glycol monoethyl ether, triethylene glycol monomethyl ether, butoxyethanol, butylene glycol monobutyl ether, dipentaerythritol, tripentaerythritol, tetrapentaerythritol, diglycerol, triglycerol, tetraglycerol, pentaglycerol, hexaglycerol, heptaglycerol and octaglycerol.

Examples of colorants include azo dyestuffs and anthraquinone dyestuffs. When the composition contains a colorant, the amount of the colorant is usually 0.01 to 1.0% by weight in the composition.

The composition of the present invention is prepared by conventional methods, for example, by mixing a PGR, PESA or its salt, a carrier and optionally auxiliaries, and further pulverization, granulation and so on. The composition of the present invention can be a variety of formulations: dry flowables (DF), liquid flowables (LF), true liquids (TL), emulsifiable concentrates (EC), dusts (D), wettable powders (WP), suspoemulsions (SE), water-dispersible granules (WG) and others. Some are registered for use only by commercial applicators using closed application systems, others are readily available for on-farm use as dusts, slurries, water soluble bags, or liquid ready-to-apply formulations.

The concentration of PESA salt is from 0.021 to 20.1 percent by volume of the composition.

The application dosage of the composition of the present invention is usually 0.01 to 10.0 kg/km$^2$, preferably 0.05 to 5 kg/km$^2$ of the amount of the PGR compound.

The method of the present invention is a new use of PESA or its salts for potentiating the effect of a PGR other than abscisic acid on a plant. The method of the present invention is a new use of PESA or its salts for protecting a plant from high doses of a PGR by a treatment of PESA or its salts. It is performed by applying PESA or its salts to plants. The plant can be any part and in any stage, for example, seed, tuber, bulb, root, leaf, stem and sprout. PESA or its salts may also be applied to surroundings of the plant, for example, soil. The soil treatment can be performed by application on the soil surface, application by mixing with soil, or the like. PESA or its salts are used in an effective amount for protecting the plant from the PGR compound. The amount of PESA or its salts used in the invention depends on the kind of the PGR compound The method can be performed by applying the PGR to plants or surroundings of the plants.

Especially suitable target plants are potato, cereals (wheat, barley, rye, oats, rice), maize (corn), sugar beet, cotton, millet varieties such as sorghum, sunflower, bean, peas, oil plants (such as canola, rape and soybean), cabbage, tomato, eggplant, pepper, and other vegetables and spices, as well as woody perennials, ornamental shrubs, turf grass, and flowers.

Suitable target crops also include transgenic crop plants of the foregoing varieties. The transgenic crop plants used according to the invention are plants, or propagation material thereof, which are transformed by recombinant DNA technology so that they are capable of synthesizing selectively acting toxins, such as, for example, from toxin-producing invertebrates, especially of the phylum Arthropoda; from *Bacillus thuringiensis* strains; from plants, such as lectins; or in the alternative, capable of expressing a herbicidal or fungicidal or abiotic stress resistance gene or capable of synthesizing a beneficial nutraceutical or pharmaceutical compound.

The compositions are particularly suited for applications on plant propagation material. The latter term embraces seeds of all kinds (fruit, tubers, grains), cuttings, cut shoots and the like. The preferred field of application is the treatment of all kinds of seeds (as specified in the target crops above), and in particular, the seed treatment of canola, maize, cereals, soybeans and other legumes and turfgrass.

A presently preferred application method of the fungicidal composition of the present invention is seed treatment. Further, a presently preferred application method of PESA or its salts in the method of the present invention is also seed treatment. In seed treatment, the application amount of the composition of the present invention is usually 1 to 200 g, preferably 5 to 100 g per 100 kg of seeds in the amount of the PGR compound.

Procedure for Treating Samples of Seed in the Laboratory

Seed was sieved with a screen of mesh size appropriate to remove broken seeds and small trash. Cracked or otherwise damaged seeds were removed. The seed was well mixed, and 50 g samples were weighed into small plastic trays. Seed treatment slurries were made by adding measured amounts of PESA or its salts and other AIs to sufficient water to bring them up to a standard volume, typically 2 ml. A fungicide (Maxim XL; Syngenta Agricultural Products, Greensboro, N.C.), a polymeric binder (CF-Clear; Becker-Underwood, Ames, Iowa), and a colorant (Color Coat Red; Becker-Underwood, Ames, Iowa) were also included in the slurry at label rates. A small aliquot of this slurry was applied to the seed using a Hege 11 coater (Wintersteiger, Salt Lake City, Utah) with a six-inch bowl at a slurry rate of 30 ounces per 100 lbs of seed. The slurry was deposited drop-wise on the spinning disk atomizer using a syringe.

After treatment, each seed sample was placed in plastic trays and dried at a room temperature for 20 to 60 minutes. The samples were then placed in small plastic bags. Samples were spot-checked using a water activity meter to make sure the water activity is below 0.7.

Alternatively, PESA salt and PGRs may be added separately to the sterile water in the growth pouch.

Pouch Assay

Seeds were placed in germination pouches consisting of germination paper hydrated with sterile water that was an insert in a gas-permeable 16×14 cm plastic pouch (CYG Pouch; Mega International, St. Paul, Minn.). In these examples, in pouch solution evaluation, PESA sodium salt or other active ingredients were added to the sterile water in the pouch. The pouches were arranged in a completely randomized block design in growth racks and placed in 19-liter polycarbonate food storage containers (Rubbermaid Commercial Products, Winchester, Va.). The sealed containers were held in an upright growth cabinet maintained at 25° C. with a 12 hour light: 12 hour dark photoperiod. When Abscisic acid was assayed in pouch studies, the pouches were first filled with sterile water to promote germination. The sterile water solutions were replaced after germination (4 days) and replaced with solutions containing ABA. After 6 days, the containers were removed from the growth cabinet, and the lengths of the roots and shoot were measured.

Hydroponic Assay:

Where hydroponically-grown rice was used in studies, the seeds were pre-incubated in water at 30° C. for 2 days to stimulate germination. Three seeds were placed on a float and cultivated hydroponically in a test tube (25 mm×200 mm), which contained 50 ml of Kimura B nutrient solution at ⅛th strength supplemented with PGRs and PESA sodium salt. The exposure of the roots to the light was prevented by wrapping the tubes with aluminum foil. The rice seedlings were incubated in a growth cabinet at 25° C. under continuous light for 14 days, and the total root length and shoot length were measured. Total root length (cm) was the root length/plant determined following scanning with WinRhizo software (Regent Instruments INC, Toronto, Canada).

The following examples are intended to illustrate the present invention and to teach one of ordinary skill in the art how to make and use the invention. They are not intended to be limiting in any way.

EXAMPLES

The following examples show that PESA reduces growth inhibition caused by high doses of the cytokinin 6-benzyladenine (6BA), the gibberellin biosynthesis inhibitor trinexapac-ethyl, the ethylene precursor 1-aminocyclopropane carboxylic acid (ACC), and the ethylene biosynthesis inhibitor aminoethoxyvinylglycine (AVG). Also, PESA potentiates 6BA reduction of lettuce seed thermodormancy.

Example 1

Lettuce that is grown for consumption during the winter months is often planted shallow and under high temperatures. Unfortunately lettuce germination is inhibited due to thermodormancy, an inhibition caused by light and high temperatures (Blaauw-Jansen, G., 1981, Physiol. Plant. 53: 553-557). Lettuce is often primed to break thermodormancy (Cantliffe, D. J., 1991, HortTechnology. 1: 95-96). However, priming is a costly and complicated procedure that requires soaking the seed in water prior to planting. Treatment of lettuce with cytokinins such as 6BA breaks thermodormancy (Cantliffe, D. J., 1991, HortTechnology. 1: 95-96), but 6BA also can reduce root growth.

To test the effect of chemical application on thermodormancy, lettuce seed was treated with PESA salt (50 g/cwt), 6BA (1 g/cwt), or a combination of PESA salt and 6BA. Lettuce seed was then grown under conditions that promote thermodormancy (33° C. and continuous light) and final seedling germination was determined (Table 1). PESA alone had no effect germination and 6BA alone stimulated germination. However, the combination of PESA and 6BA stimulated germination more the 6BA alone (82.5% vs. 62.0%, respectively). This shows that PESA potentiates 6BA germination promotion of lettuce.

To test the effect of chemical application on root growth, lettuce seed was treated with PESA salt (50 g/cwt), 6BA (1 g/cwt), or a combination of PESA salt and 6BA. Treated lettuce seed was grown at 25° C. in darkness, and root lengths were determined after 3 days. PESA alone had no effect on lettuce root growth, while 6BA alone reduced root growth (Table 1). However, the combination of PESA and 6BA stimulated root growth compared to 6BA alone. This shows that PESA safened the 6BA application.

Taken together, this example shows that PESA can be used not only to potentiate 6BA induced lettuce germination, but also to reduce the negative effects of 6BA on root growth.

TABLE 1

Effect of PESA salt and 6BA alone and in combination on germination and root growth of lettuce.

| PESA salt | Germination (%) | | Root length (cm) | |
| --- | --- | --- | --- | --- |
| (g/cwt) | 0 g/cwt 6BA | 1 g/cwt 6BA | 0 g/cwt 6BA | 1 g/cwt 6BA |
| 0 | 12.1 | 66.0 | 3.7 | 3.1 |
| 50 | 14.9 | 82.5 | 3.8 | 3.4 |

Example 2

In pouch solution evaluation, the cytokinin 6BA reduced the main root length of cotton seedlings (Table 2). PESA salt increased root length in a dose-dependent manner. The combination of 10 or 30 mg/liter PESA with 1 or 10 mg/liter 6BA reduced root growth inhibition caused by 6BA.

This shows that PESA salt also safened cotton against root growth inhibition induced by 6BA.

TABLE 2

Effect of PESA salt and 6BA on root length (cm) of cotton.

| | 6BA (mg/liter) | | | |
| --- | --- | --- | --- | --- |
| PESA salt (mg/liter) | 0 | 1 | 10 | 100 |
| 0 | 9.8 | 8.9 | 8.5 | 4.6 |
| 3 | 9.8 | 6.5 | 8.3 | 4.3 |
| 10 | 11.9 | 10.5 | 9.7 | 4.4 |
| 30 | 13.0 | 11.7 | 10.4 | 4.7 | n = 8 replicate pouches of 3 seedlings/pouch per treatment.

Example 3

In pouch solution evaluation, treatment with the gibberellin biosynthesis inhibitor trinexapac-ethyl on rice cv. Cheniere had a negative effect on main root length (Table 3). PESA salt increased root length in a dose-dependent manner. The combination of 3, 10, or 30 mg/liter PESA with 1 or 10 mg/liter trinexapac-ethyl reduced root growth inhibition caused by trinexapac-ethyl.

This shows that PESA salt safened rice against root growth inhibition induced by trinexapac-ethyl.

TABLE 3

Effect of PESA salt and trinexapac-ethyl
on root length (cm) of rice cv. Cheniere.

| PESA salt (mg/liter) | Trinexapac-ethyl (mg/liter) | | | |
|---|---|---|---|---|
| | 0 | 1 | 10 | 100 |
| 0 | 11.1 | 10.9 | 9.9 | 5.0 |
| 3 | 12.1 | 11.4 | 10.3 | 5.1 |
| 10 | 12.5 | 11.5 | 10.2 | 5.0 |
| 30 | 13.1 | 12.0 | 10.2 | 5.0 | n = 8 replicate pouches of 3 seedlings/pouch per treatment.

Example 4

In pouch solution evaluation on rice seedlings, treatment with 1, 10, or 100 mg/liter of the ethylene precursor ACC alone reduced root length (Table 4). PESA salt increased root length. Except for the combination of 10 mg/liter PESA with 1 mg/liter ACC, the combination of 3, 10, or 30 mg/liter PESA with 1, 10, or 100 mg/liter ACC reduced root growth inhibition caused by ACC.

This shows that PESA salt safened rice against root growth inhibition induced by ACC.

TABLE 4

Effect of PESA salt and ACC on root
length (cm) of rice cv. Cheniere.

| PESA salt (mg/liter) | ACC (mg/liter) | | | |
|---|---|---|---|---|
| | 0 | 1 | 10 | 100 |
| 0 | 9.3 | 8.8 | 7.8 | 4.3 |
| 3 | 9.7 | 9.3 | 8.4 | 4.5 |
| 10 | 9.8 | 8.0 | 8.4 | 4.6 |
| 30 | 9.4 | 9.8 | 9.0 | 5.0 | n = 8 replicate pouches of 3 seedlings/pouch per treatment.

Example 5

In pouch solution evaluation on rice seedlings, treatment with the aminoethoxyvinylglycine (AVG), an inhibitor of ethylene biosynthesis, increased root growth at 0.1 mg/liter, but reduced root growth at 10 or 100 mg/liter (Table 5). PESA salt alone increased root length. The combination of 3 mg/liter PESA with AVG had little effect on root growth. However, 30 mg/liter PESA combined with 0.1 mg/liter enhanced root growth and combined with 1 or 10 mg/liter educed root growth inhibition caused by AVG.

This shows that PESA salt safened rice against root growth inhibition induced by AVG.

TABLE 5

Effect of PESA salt and AVG on root
length (cm) of rice cv. Cheniere.

| PESA salt (mg/liter) | AVG (mg/liter) | | | |
|---|---|---|---|---|
| | 0 | 0.1 | 1.0 | 10 |
| 0 | 10.9 | 11.5 | 8.6 | 3.5 |
| 3 | 11.4 | 11.6 | 8.2 | 3.7 |
| 30 | 12.3 | 12.7 | 9.3 | 4.0 | n = 8 replicate pouches of 3 seedlings/pouch per treatment.

PESA does not counteract the growth inhibiting effects of all PGRs. The following example shows that PESA does not reduce growth inhibition by abscisic acid (ABA).

Example 6

In a pouch solution evaluation on cotton seedlings, treatment with the abscisic acid (ABA) inhibited root growth (Table 6). Combinations of PESA (3 or 10 mg/liter) did not reduce root growth inhibition caused by ABA.

TABLE 6

Effect of PESA salt and ABA on root length (cm) of cotton

| PESA salt (mg/liter) | ABA (mg/liter) | | |
|---|---|---|---|
| | 0 | 1 | 10 |
| 0 | 11.6 | 10.4 | 10.0 |
| 3 | 11.9 | 10.1 | 9.6 |
| 10 | 11.1 | 10.4 | 9.2 |

The invention claimed is:

1. A composition for enhancing plant growth comprising N-(phenylethyl) succinamic acid (PESA) or its salts and a plant growth regulator,
   wherein the plant growth regulator is selected from the group consisting of
   a cytokinin at a ratio of PESA:cytokinin of from about 1:1 to about 50:1,
   a gibberellin biosynthesis inhibitor at a ratio of PESA: gibberellin biosynthesis inhibitor of from about 1:1 to 30:1,
   an ethylene inducer at a ratio of PESA:ethylene inducer of from about 0.3:1 to 30:1, and
   an ethylene inhibitor at a ratio of PESA:ethylene inhibitor of from about 0.3:1 to 30:1.

2. The composition according to claim 1 where the N-(phenylethyl)succinamic salt is sodium.

3. The composition according to claim 1 where the plant growth regulator is a cytokinin.

4. The composition according to claim 3 where the cytokinin is 6-benzyladenine.

5. The composition according to claim 1 where the plant growth regulator is a gibberellin biosynthetic inhibitor.

6. The composition according to claim 5 where the gibberellin biosynthetic inhibitor is trinexapac-ethyl.

7. The composition according to claim 1 where the plant growth regulator is an ethylene inducer.

8. The composition according to claim 7 where the ethylene inducer is 1-aminocyclopropane carboxylic acid.

9. The composition according to claim 1 where the plant growth regulator is an ethylene inhibitor.

10. The composition according to claim 9 where the ethylene inhibitor is aminoethoxyvinylglycine.

11. The composition according to claim 2 wherein the concentration of the N-(phenylethyl)succinamic acid salt is from 0.021 percent to 20.1 percent by volume of the composition.

12. A method of enhancing the growth of plants by applying an effective amount of the composition of claim 1 to seeds or the root zone of seedlings or plants.

13. The method according to claim 12 where the composition is applied to seeds.

14. The method according to claim 12 where the composition is applied to lettuce seed to promote germination.

15. A method for enhancing the growth of plants when plant growth regulators are used which comprises applying N-(phenylethyl)succinamic acid (PESA) or its salts in combination with a plant growth regulator to a plant or soil,
wherein the plant growth regulator is selected from the group consisting of
a cytokinin at a ratio of PESA:cytokinin of from about 1:1 to about 50:1,
a gibberellin biosynthesis inhibitor at a ratio of PESA: gibberellin biosynthesis inhibitor of from about 1:1 to 30:1,
an ethylene inducer at a ratio of PESA: ethylene inducer of from about 0.3:1 to 30:1, and
an ethylene inhibitor at a ratio of PESA:ethylene inhibitor of from about 0.3:1 to 30:1.

* * * * *